United States Patent
Ischinger

[11] Patent Number: 6,146,417
[45] Date of Patent: Nov. 14, 2000

[54] TUBULAR STENT

[76] Inventor: Thomas Ischinger, Oberonstrasse, 3, 81927 Munich, Germany

[21] Appl. No.: 09/242,852
[22] PCT Filed: Aug. 22, 1997
[86] PCT No.: PCT/EP97/04585
§ 371 Date: Jun. 25, 1999
§ 102(e) Date: Jun. 25, 1999
[87] PCT Pub. No.: WO98/07386
PCT Pub. Date: Feb. 26, 1998

[30]       Foreign Application Priority Data

Aug. 22, 1996 [DE] Germany ............... 196 33 901

[51] Int. Cl.[7] ............................................. A61F 2/06
[52] U.S. Cl. ............................ 623/1.15; 623/1.1
[58] Field of Search ................. 623/1, 1.15, 1.16, 623/1.1, 1.12, 1.18, 1.19, 1.2, 1.21

[56]            References Cited

U.S. PATENT DOCUMENTS 5,019,090   5/1991   Pinchuk .
5,443,498   8/1995   Fontaine .

FOREIGN PATENT DOCUMENTS

| 0 565 251 A1 | 10/1993 | European Pat. Off. . |
| 0 790 041 A3 | 8/1997 | European Pat. Off. . |
| 0 795 304 A1 | 9/1997 | European Pat. Off. . |
| 44 32 938 A1 | 3/1995 | Germany . |
| 93 21 136 U1 | 6/1996 | Germany . |
| WO 95/31945 | 11/1995 | WIPO . |
| WO 96/33672 | 10/1996 | WIPO . |

*Primary Examiner*—Michael Buiz
*Assistant Examiner*—Anthony King
*Attorney, Agent, or Firm*—Larson & Larson, P.A.; James E. Larson

[57]            ABSTRACT

A stent is formed in a tube like grid structure which consists of at least one sequence (i.e., one tubular segment) of closed loop elements which are connected to each other at at least one connecting point per loop (the loop contact point) wherein either the opposing ends of each sequence are circumferentially connected or one sequence is helically wrapped around the longitudinal axis of the stent.

14 Claims, 8 Drawing Sheets

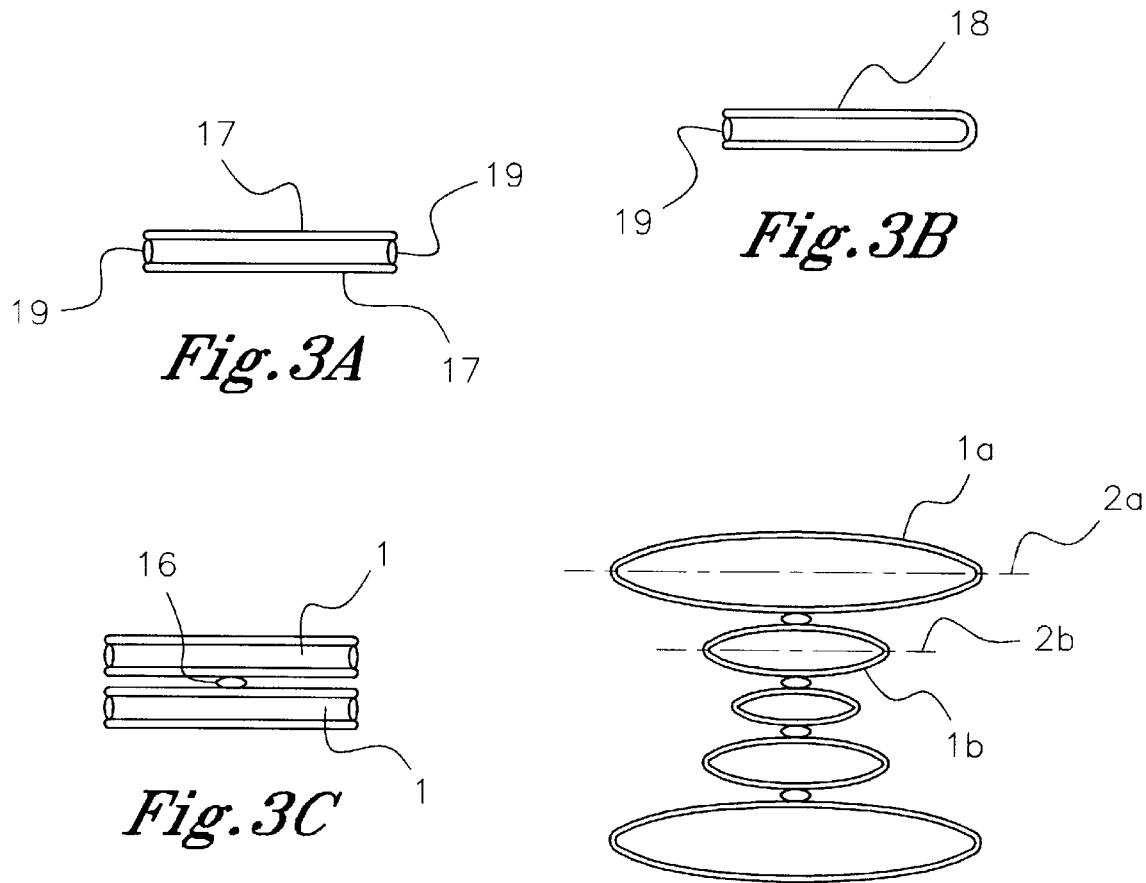
*Fig.3A*
*Fig.3B*
*Fig.3C*
*Fig.4A*
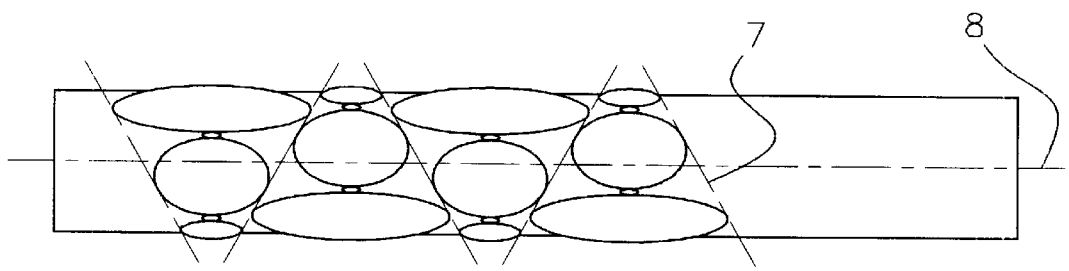
*Fig.4B*

TUBULAR STENT

PRIOR APPLICATIONS

This application is a §371 U.S. national phase application of PCT/EP97/04585, filed Aug. 22, 1997, which was an international application of German patent application 196 33 901.4, filed Aug. 22, 1996.

BACKGROUND OF THE INVENTION

1. Field of Invention

This invention relates to stents. More particularly, it relates to stents formed from ring elements for providing a highly flexible, low profile stent which is easy to manufacture.

2. Description of the Prior Art

Stents are used as support devices for tubular organs, in particular blood vessels. Current stent devices include the Palmaz Schatz, Boneau, Fontaine, Fogerty, Hilisted, Williams, Gianturco Roubin, Gianturco self-expanding stent, to name some.

U.S. Pat. No. 5,443,498 discloses a vascular stent that includes a continuous wire which is formed into a substantially tubular body having a plurality of oblong, open cells which are staggered around the circumference of the tube. When the tubular stent body is formed in its unexpanded state, the long sides of each oblong cell are arranged substantially parallel to the longitudinal axis of the tubular body. Adjoining cells may then be bonded together at a point between adjacent parallel sides on a cell.

German Patent No. 44 32 938 A1 discloses a tubular or cylindrical shaped endoprosthesis which is applied to a blood vessel by using a balloon catheter. The endoprosthesis consists of a string formed by flexible segments which are substantially arranged in a wave form and in a uniform manner along a helical line.

Conventional zig zag stents have to be rather short because the straight wire segments prevent the stent from easy adaption to curves in the cavities or openings in the patient's body. Furthermore, the expansion forces of customary stents decrease with the length of the stent. An attempt to overcome these drawbacks is the combination of a plurality of short stents connected to one another at their ends. Although these modified stents have better characteristics for certain applications, there is nevertheless still a need for elongated, self-expanding stents which combine the above mentioned characteristics with a better functioning.

Furthermore, a control of the deformation of the stent after self or balloon expansion is strongly desired. U.S. Pat. No. 5,019,090 discloses the manufacturing of a helical stent which consists of wrapping a wire around a cylindrical core in a helical manner. In this case, all segments of the stent have the same length which leads to the drawback that the stent deforms in a undesirable manner after radial compression because the angle bisector of the angle between each pair of segments does not extend parallel to the center axis of the stent. German Patent No. 93 21 136 U1 discloses a way of manufacturing a stent which overcomes this problem and which has the desired feature of a controllable deformation. Finally, it should be noted that all of the above mentioned stents have in common that they are manufactured from a single continuous wire.

From the foregoing, it can be seen that the ideal vascular prosthesis should include several features: easy manufacturing, high flexibility, low profile, little material as possible, radial strength, high expansion rate, firm seating on application instrument, little recoil after expansion, no shortening upon expansion, versatility for use in different anatomies and usable as a balloon and self-expanding stent (depending on use of high or low memory material).

SUMMARY OF THE INVENTION

It is thus an object of the present invention to provide a stent that combines all of the needed requirements in a unique manner. The use of single closed loop elements for the proposed stent lends extreme stability and radial strength and ensures low risk of disintegration of the stent structure as seen with stents formed out of zig zag wires. Use of closed loop elements permits variations in structure, strength, configuration and physical properties of the stent by simple design changes. Alignment of closed loops permits use of different materials in one circumferential series of loop elements, which permits modifications of the physical properties of stent segments within a stent, thus rendering the stent more adaptive to the properties of target vessels.

The stent of the present invention is formed in a grid structure comprising of at least one closed loop, made of conventional material. The loop either itself, or in combination with further loops, is formed in a tube-like shape. A single loop element is thus formed such that only round passages and curves occur, thereby eliminating sharp edges and borders. If a plurality of such closed loop elements is used, the loops are attached to each other by welding, soldering, gluing or similar technique. This leads to an advantage that different materials can be combined, in contrast to the prior art, where only one material is used. For example, it is possible to use a material having spring like qualities for some loops and a material which is plastically deformable for the other loops. The result is a stent having springlike sections and plastically deformable sections. This type of novel stent can then be used for a variety of applications.

DESCRIPTION OF THE DRAWINGS

The invention may be best understood by those having ordinary skill in the art by reference to the following detailed description when considered in conjunction with the accompanying drawings in which:

FIG. 3A shows a loop element consisting of two parallel wires with a suitable connection of their ends.

FIG. 3B shows a loop element made of a U-shaped wire with only one connection between the adjacent ends of the wire.

FIG. 3C shows a sequence of two loop elements each of which has a connecting point in its midportion.

FIG. 4A shows a tubular segment consisting of loop elements which have different length in the longitudinal direction.

FIG. 4B shows a stent which consists of the tubular segments of FIG. 4A.

DETAILED DESCRIPTION OF THE PREFERRED EMBODIMENT

Figure 1A:
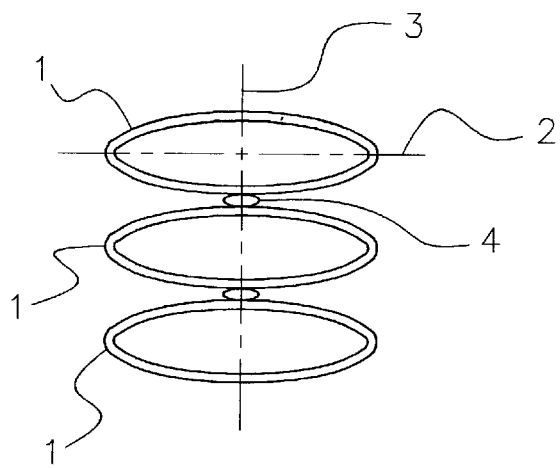
FIG. 1A shows a side view of a tubular segment of the unexpanded stent consisting of three closed loops in an circumferential arrangement.
Figure 1B:
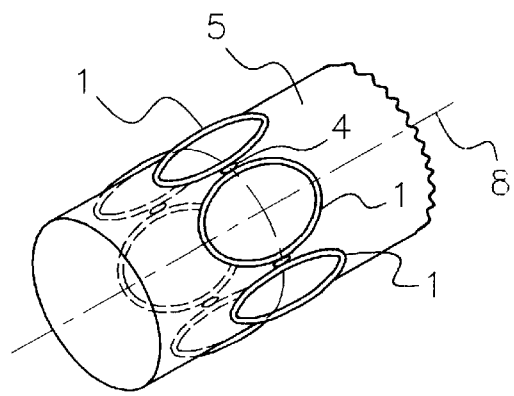
FIG. 1B shows a perspective view of an expanded stent consisting of an annular successive sequence of loop elements which are interconnected at one point.
Figure 1C:
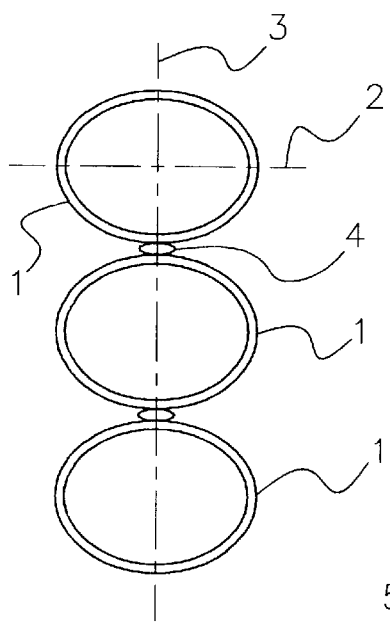
FIG. 1C shows the tubular segment of FIG. 1A in the expanded state.

FIGS. 1A and 1C show a tubular segment of a stent according to the invention which consists of single closed loops 1 in the unexpanded and expanded state, respectively. Each loop 1 is connected at a interconnection 4 with an adjacent loop 1. FIG. 1B shows the stent 5 which consists of a longitudinal sequence with respect to the longitudinal axis 8 of the stent 5. Possible variations of this stent structure are described below.

Figure 5A:
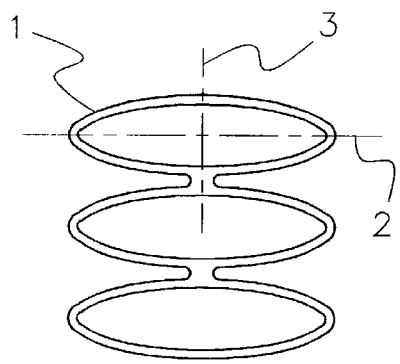
FIG. 5A shows a tubular segment with the loops being symmetrical about their major and minor axes as in an ellipse.

The stent 5 consists of single loops 1 or sequences of loops 1 which have an oval or circular cross section (see FIGS. 1A and 5A) and which are arranged in circumferential or longitudinal direction, 3 and 2 respectively, having at least one interconnection 4. The single loops 1 may be formed with round wire by connecting its ends through, for example, welding, soldering and gluing, or they may be cut from tubes or flat material.

The originally formed loop element 1 can correspond to a compressed, i.e. unexpanded, form (small diameter of the stent) or to a completely expanded form (large diameter of the stent). Depending on the material and its strength it may be more suitable for the manufacturing process and the physical characteristics of the stent to fold a basic form (which corresponds to the expanded or partly expanded diameter of the stent) on a balloon of a balloon catheter or to compress it or to fold a basic form (which corresponds to the compressed diameter) on the balloon. In the latter case, the stent or its loop is deformed far beyond its basic form. In the first case, it is only partly deformed beyond its basic form or not deformed at all. The diameter of the basic stent form or its loop form is substantial for the deforming characteristics and the collapse resistance of the expanded stent.

The number of loops 1 of a sequence in the circumferential direction 3 (which is the expanding direction) depends on the necessary diameter of the expanded stent (for the maximum expansion of the stent for a predetermined vessel diameter). Furthermore, it depends on the acceptable contraction of the whole structure. In addition to the strength of the material, the number of loops 1 in the circumferential direction determines the collapse resistance of the stent 5. The collapse resistance also partly depends on the opening angle of the sides of the single loops which open on expansion. The recoil of the expanded loop is smaller for larger opening angles than for smaller opening angles.

The substantial variables for the modification of the stent's characteristics are the number of loops, the material used, the combination of loops made of different material, the strength of the material, and the opening angles of the sides of the loops during the (implanted and partly expanded) functional state of the stent.

The basic form of a sequence of loops 1 may also be formed by parallel extending pairs of wire 17 (see FIG. 3A) or a single U-shaped wire 18 (see FIG. 3B) and in that the ends 19 are connected by a suitable connection. The resulting wire loop 1 is connected to the next wire loop at a point 16 preferably in the midportion of the U-shaped ends (see FIG. 3C).

Figure 2:
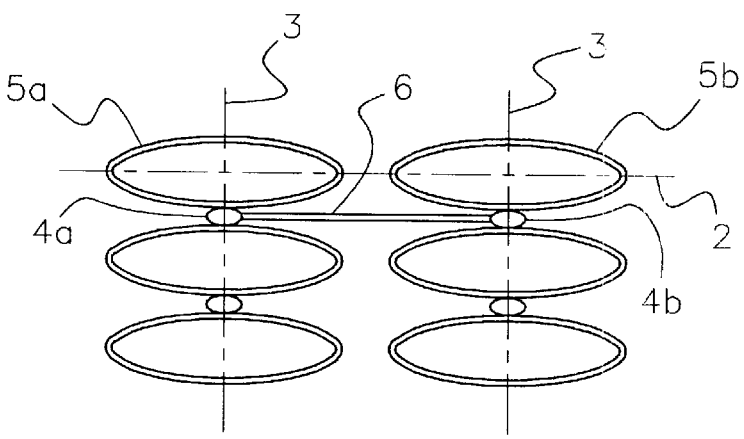
FIG. 2 shows two adjacent tubular segments which are interconnected by a backbone.

In an alternate embodiment, as seen in FIG. 2, a sequence or chain of loop elements 5a and 5b can form a very short stent structure by connecting their ends in a circumferential direction. An arbitrary length of the stent can be obtained by lining up such tubular segments in longitudinal direction with or without connecting them at discrete points by a backbone 6. A loop sequence in longitudinal direction can also be used as the basic element in that sequences with the same length lined up in a circumferential direction and connected with the adjacent loop elements in a circumferential direction.

Figure 5B:
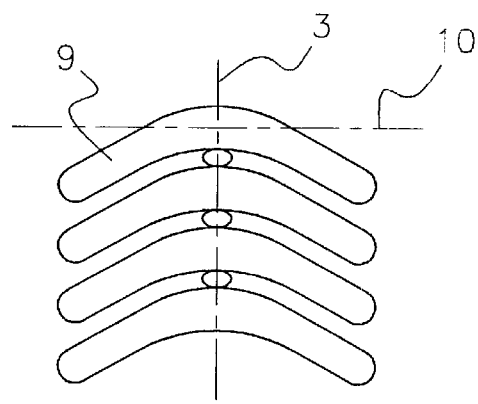
FIG. 5B shows a tubular segment with the loops having a banana like shape thus being asymmetrical about a longitudinal midline along their major axes when unexpanded.
Figure 5C:
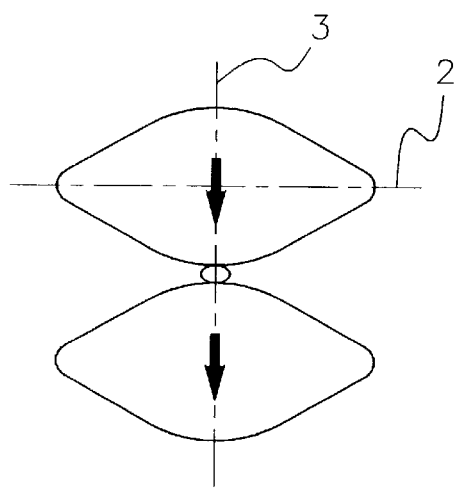
FIG. 5C shows the tubular segment from FIG. 5B being symmetrical about a longitudinal midline along their major axes when expanded.
Figure 6A:
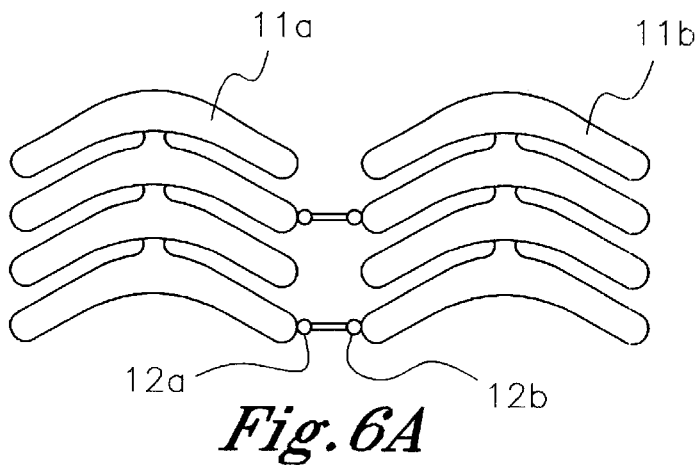
FIG. 6A shows two adjacent tubular segments which are interconnected in such a way that the connecting points are arranged at the ends of the banana like shaped loops along a longitudinal line parallel to the longitudinal axis of the stent.
Figure 6B:
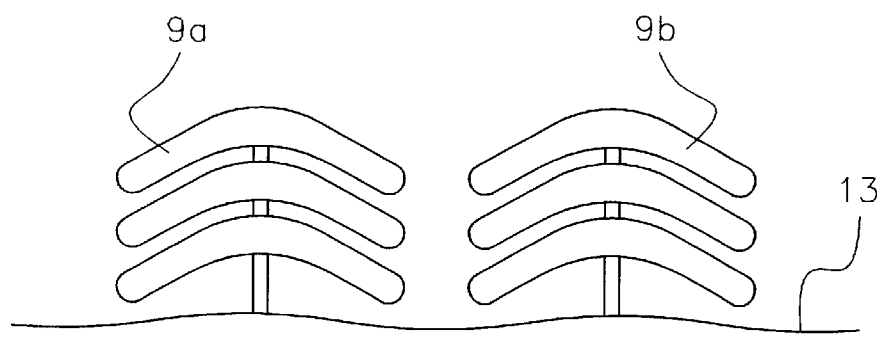
FIG. 6B shows two adjacent tubular segments which are interconnected by a backbone which is arranged along a sinusoidal line parallel to the longitudinal axis of the stent.

In FIG. 5B the loop element 9 is asymmetrical about a longitudinal midline 10 along the major longitudinal axis to form-loop elements 9a, 9b, 11a and 11b, as shown in FIGS. 6A and 6B, having a half moon or banana shape. In this configuration of loops 9, the length of the minor circumferential axis 3 increases without significant decrease of the length of the major longitudinal axis 2 until substantial symmetry about the longitudinal midline 10 is reached. As shown in FIG. 6A two tubular segments 11*a*, 11*b* are connected by connecting at least two longitudinally adjacent ends of the major longitudinal axis of the loop elements so that connecting points 12*a*, 12*b* (FIG. 6*a*) are arranged along a longitudinal line parallel to the longitudinal axis 8, of the stent. Asymmetrical closed loop elements 9*a* and 9*b* are interconnected longitudinally by a sinusoidal longitudinal element 13.

Figure 7A:
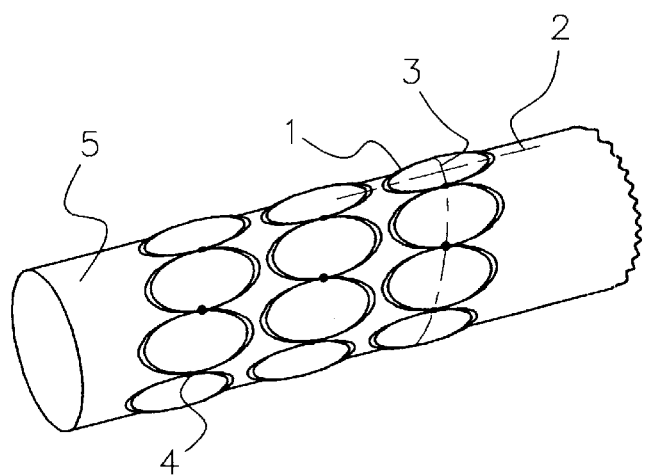
FIG. 7A shows a stent which has been manufactured by arranging the loop elements helically around a cylinder.
Figure 7B:
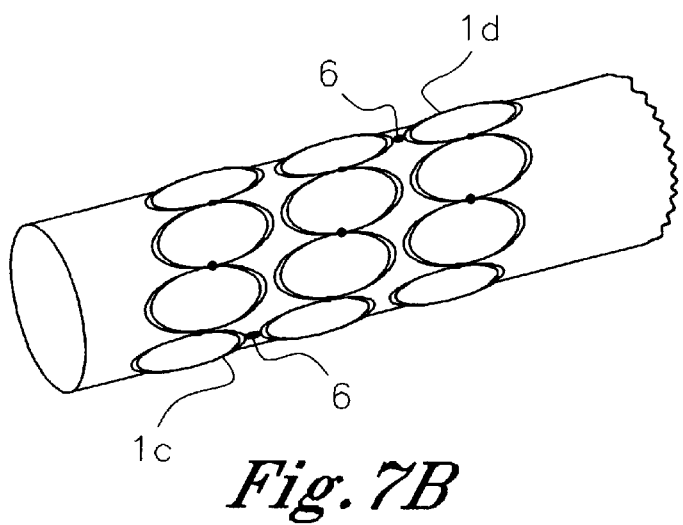
FIG. 7B shows the stent from FIG. 7A wherein only the first and the last loop elements are connected to an adjacent loop element on an adjacent helical turn.
Figure 7C:
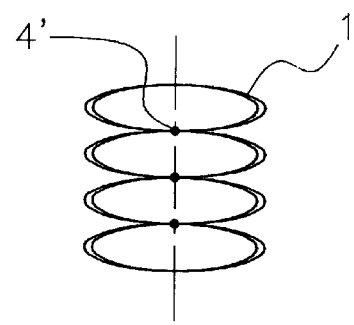
FIG. 7C shows the loop elements being interconnected at their midportions to form a chain.
Figure 7D:
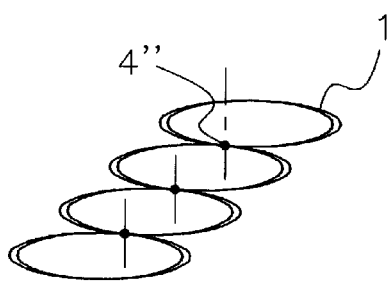
FIG. 7D shows the loop elements being interconnected outside of their midportions to form a chain.
Figure 7E:
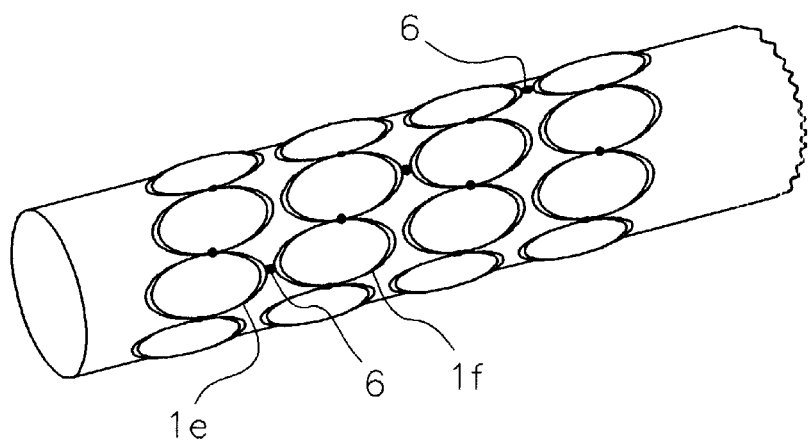
FIG. 7E shows the stent from FIG. 7B but with more loops being connected to an adjacent loop element on an adjacent helical turn.
Figure 8A:
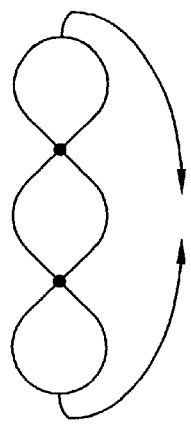
FIG. 8A shows a closed loop element which is segmented by connecting the opposing loop sides at two points.
Figure 8B:
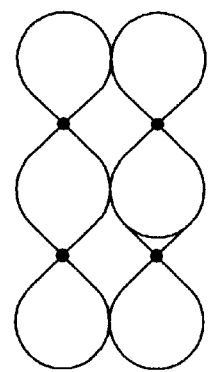
FIG. 8B shows a longitudinal arrangement of loop elements from FIG. 8A
Figure 8C:
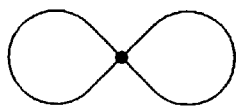
FIG. 8C shows a horizontally segmented loop element.
Figure 8D:
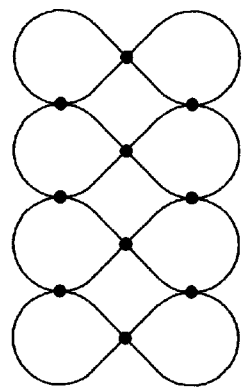
FIG. 8D shows a circumferential sequence of loop elements from FIG. 8C.
Figure 9A:
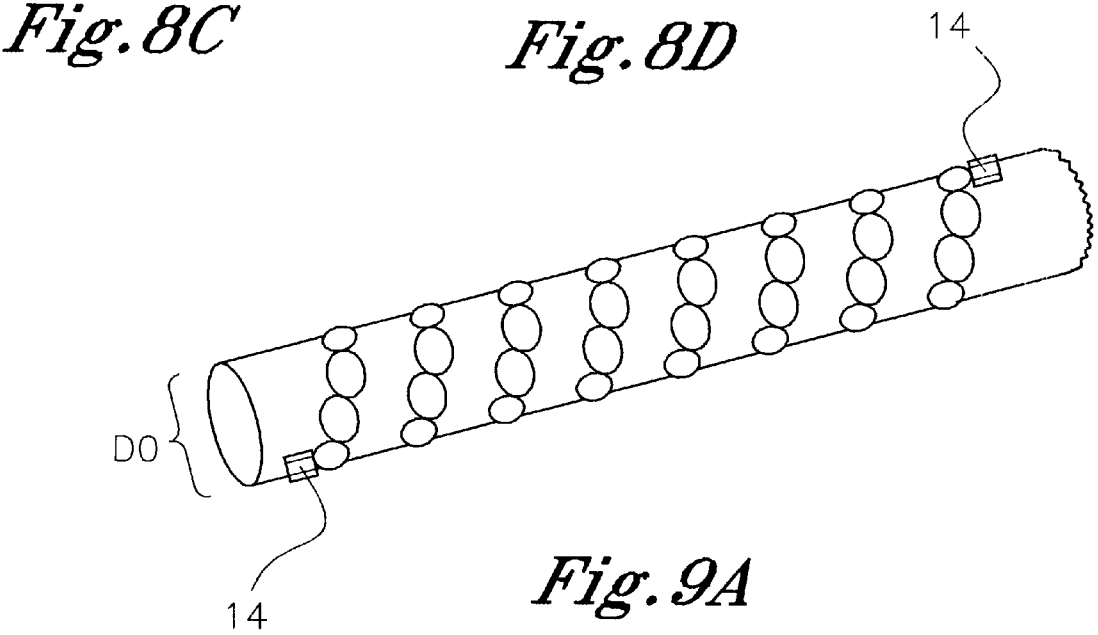
FIG. 9A shows the stent from FIG. 7A being kept in its unexpanded state by a mechanism which exerts longitudinal or circumferential traction.
Figure 9B:
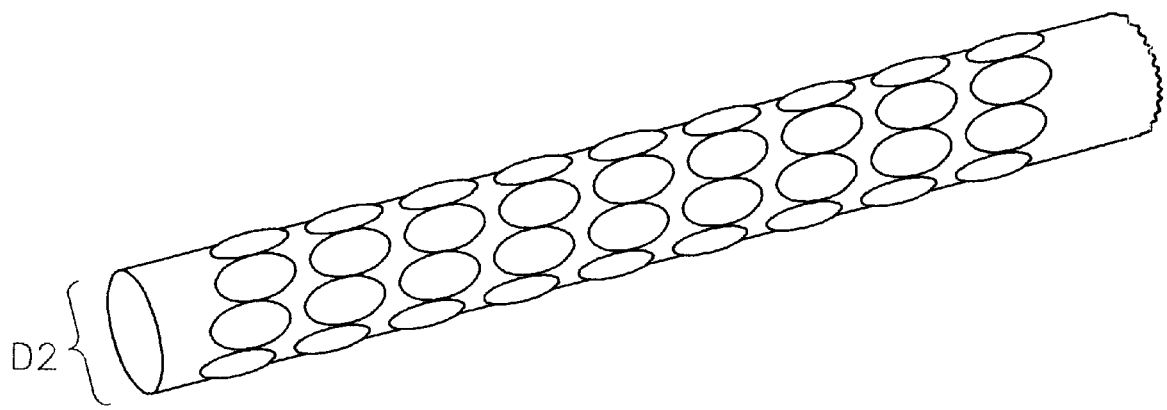
FIG. 9B shows the stent from FIG. 9A after expansion.

In a second alternate embodiment, as shown in FIG. 7A, instead of lining up tubular segments (i.e. sequences of single loops), a helical wrapping of a chain of single loops can lead to a similar (very long, if desired) stent structure. The ends of the loop chains do not have to be connected but they may be connected 4' or 4" with the adjacent loop element 1*c*, 1*d*, 1*e*, 1*f* in the longitudinal direction 2 by the backbone 6, as seen in FIGS. 7B and 7E. This helical configuration is very flexible in the longitudinal direction 2 and leads to a good seating on the balloon or a similar dilatation elements. Both, the first and second alternate embodiments have portions of stent structures that extend more parallel and portions that extend more vertical to the longitudinal axis of the vessel.

In a third alternate embodiment, a single loop which is sufficiently large and which has a sufficient side length in circumferential direction can be wrapped circularly (with interconnected U-shaped ends) or helically (without interconnected ends) around the balloon or the dilatation element. In the first case, (i.e. with a circular wrapping and connected U-shaped ends), wave like configured loop sides are used to keep the expansion ability of the structure during (balloon) dilatation.

In the case of a helical wrapping of the loops around the dilatation element, the loop sides can extend in a wave like manner. A particular embodiment of the helical wrapping is a change of the winding direction at least once after at least 360 degrees in the same direction.

The helical configurations have a particularly good seating on the balloon (dilatation element) and a large flexibility. Preferably the stent structure does not extend parallel to the axis of the vessel but helically or circumferentially.

If the loop sequences are not connected to the adjacent sequences in a longitudinal direction already during manufacturing, the loop chains can be connected in the longitudinal direction by conventional soldering, gluing, welding, laser, electro and other methods. If a shortening of the total length of the stent shall be minimized during stent expansion, a particular connection of adjacent loop sequences in the longitudinal direction is desirable. To this end, it is not the adjacent free loop sides which are connected, but the connection being made at at least one contact point of the single loop elements with a separate connector. Thus, a fixed distance spacing is obtained between the loop sequences which are connected in longitudinal direction during expansion of the stent structure. This spacing connection can be formed always at the same circumferential position (e.g., always at 6 o'clock), in form of a continuous connection (e.g., wire) corresponding to a backbone which leads to a high flexibility, in alternating positions (e.g., 6 o'clock, 12 o'clock, 6 o'clock and other changes of position) or leaving out certain sequences (less effective for keeping the spacing). The spacing connection or the above mentioned separate connector is made of very flexible material (e.g., thin wire). Thus the length flexibility of the stent is better than the one which is obtained by using connections of the loops with soldering, welding, etc.

Figure 5D:
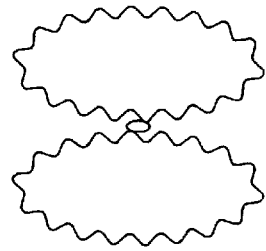
FIG. 5D shows a tubular segment with the loops having a wave like shape.

Particular configurations of the single loop elements can be used for additional ends. Instead of an even extension of the material which forms the loop (e.g., wire), this material can also extend in a wave like form and a single loop or a sequence of loops may have a flower or star-like structure, as shown in FIG. 5D. This structure allows isolated expansion of a single loop, e.g., for the passage of a catheter through a loop in a side wing for the dilatation of a side wing stenosis.

Figure 5E:
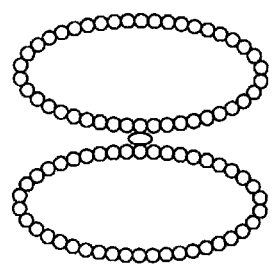
FIG. 5E shows a tubular segment with the loops consisting of small circles.

Furthermore, a single loop or all single loops in connection with a sequence of loops in the circumferential direction (expansion direction) can have a (nonexpanded) wave like basic form (see FIG. 5D), so that the shortening of the stent in the longitudinal direction is minimized during expansion of the sequence of loops. This wave like structure of a sequence of loops does not have to be (but may be) obtained by a special folding of another basic structure, but may be partly or solely manufactured as such as a basic structure. Such an expanded single loop or a single ring may also consist of a chain of loops or small rings (see FIG. 5E).

The loop structure according to the invention is useful as mentioned for purely spring elastic stent materials and also for stent materials which are plastically deformable beyond their limit of elasticity.

Figure 10A:
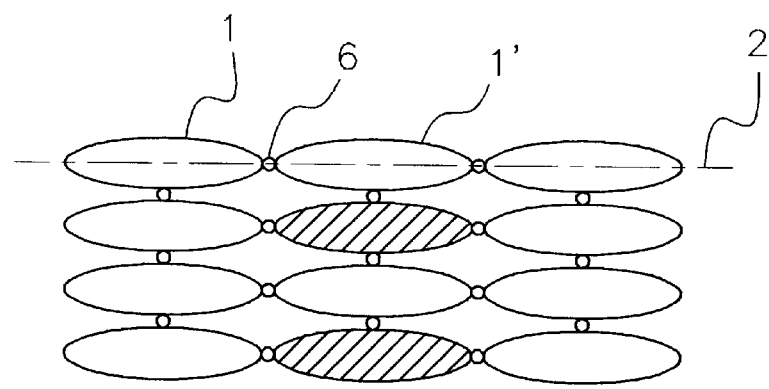
FIG. 10A shows three longitudinally arranged tubular segments wherein at least one loop element has a different functional material property in comparison to the others.
Figure 10B:
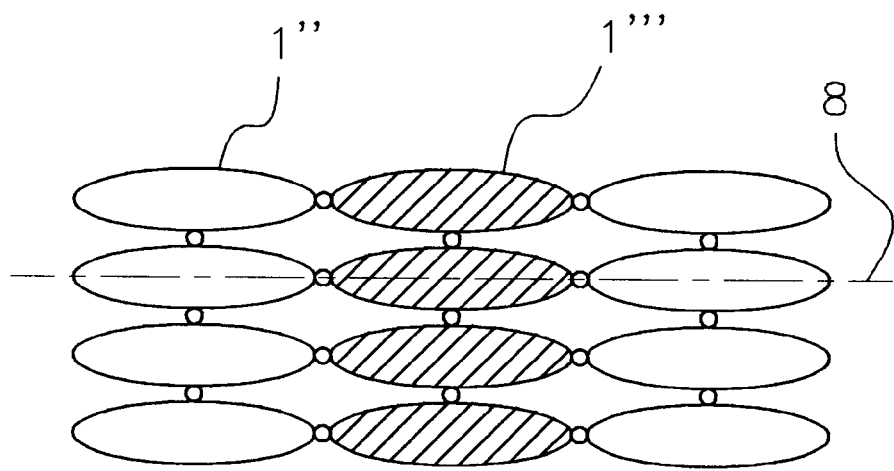
FIG. 10B shows three longitudinally arranged tubular segments wherein balloon expandable tubular segments alternate along the longitudinal axis of the stent with self-expandable tubular segments.
Figure 11:
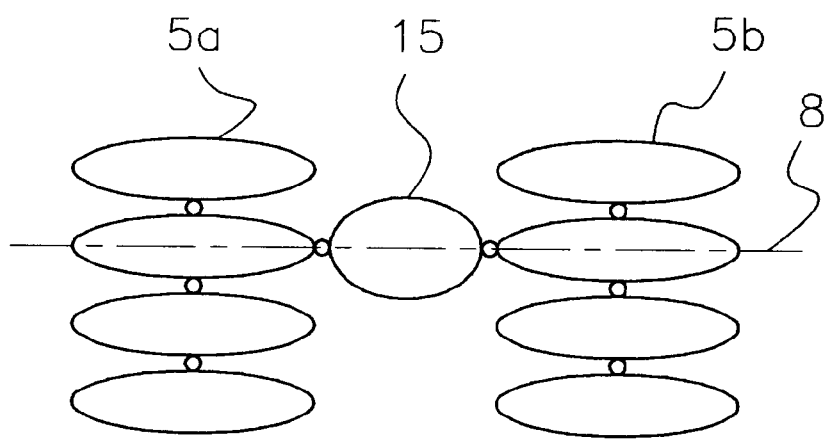
FIG. 11 shows two longitudinal arranged tubular segments which are interconnected in the longitudinal axis by a closed loop element.

Sequencing of segmented (see FIGS. 8A through 8D) or unsegmented (see FIGS. 1A through 1C) single loops in the circumferential direction 3 for the manufacturing of a stent leads to the possibility to use different materials in a stent or in a loop or ring sequence. Thus a circular sequence of loops can be formed which are made of plastically deformable and spring elastic material, as shown in FIGS. 10A and 10B. At least one loop 1' of a sequence in the circumferential direction may consist of a different material and/or have different characteristics compared to the other loops of the sequence.

The sequence of loops which follows in the longitudinal direction may contain the different loop 1" and 1'" at the same (e.g., 6 o'clock to 6 o'clock) or at a different position (e.g., 6 o'clock to 8 o'clock) position. Thus, modifications of the characteristics of the stent, with mainly spring elastic characteristics, may be obtained by using plastically deformable loops and visa versa. These combinations lead to new applications and versatility.

A mixture of materials may also be used in large single loops or in a helical configuration of sequences of loops.

In a balloon expandable stent, the stent is premanufactured with a certain first inner diameter and are applied to the dilatation element either during the manufacturing process or by the medical staff. Then they are compressed to a smaller diameter (D0) either manually or by using a compression tool 14 depending on the stent or the diameter of the balloon catheter. During expansion of the dilatation element the stent is expanded to a large diameter (D2) and will be left at the desired position after taking away the application system. A single short closed loop stent, a sequence of single unconnected closed loop stents and closed loop stents which are connected in the longitudinal direction are applied in the same manner. Helical stents are preferably delivered in finished helical form and with the above mentioned inner diameter, or they are already applied to the balloon catheter or the dilatation element with the inner diameter (D0). Helical stents may also be provided in an unhelical form and may be wrapped on the dilatation element by the medical staff.

The stent may already be applied to the dilatation element and may have a protection cover which can be drawn away during the surgery to avoid the loss of the stent during the application.

Self-expanding stents have to be kept on the dilatation element or on the application system (without a dilatation possibility) in a compressed and fixed state (inner diameter D0), for example, by gluing, tying (with a rated breaking point of the retaining thread), or by using other retaining mechanisms 14 which are connected to release mechanisms. Self-expanding stents are preferably pre-applied.

A stent material made of a temperature memory alloy may ease the application of self-expanding stents to the application system or dilatation element.

Helical stents can be kept with a small diameter and fixed on the application system or dilatation element by applying a mechanical traction which acts in longitudinal direction. Release, for example, cutting the retaining thread or breaking the retaining system (thread, gluing etc . . . ), during the balloon expansion (in case the application system is a dilatation element or a balloon) lets the helical stent jump to its functional diameter. Thus the total length of the stent may decrease. This shortening may be balanced in that the single rings or loops which make up the helical structure are also compressed and take their basic form (loop or ring form) after release of the retaining mechanism through self-expansion. This configuration is far superior to pure coil configurations.

Use of at least one spring elastic loop 15 in a preferably circumferential (but also in the longitudinal direction) sequence of plastically deformable (and conventional balloon expandable) rings can improve the characteristics of the stent (e.g., smooth and continuing self-expansion of a balloon expandable stent after application). Or, visa versa, a self-expandable stent can be balloon expanded in its end section (D2) by using plastically ring elements in a preferably spring elastic stent.

The purely plastically deformable loop elements can be arranged in such a way that they keep the single spring elastic elements or the sequences of spring elastic elements in a compressed form.

With regards to the novel stent of the present invention, it can now be seen that certain advantages exit. These include: (1) versatile usage of a basic structure with easy manufacturing; (2) high flexibility of the stent and thus useful for complex surgeries, difficult anatomy of the vessel, e.g., vessel curves and for very long stenosis; (3) convenient relation between free surface and surface which is covered with material which is easy to vary by changing the number of the loops in a sequence; (4) loop design without sharp edges, protruding wires, even if the stent is not manufactured of round wire material as its basic form; (5) easy modification in the manufacturing leads to a narrow or a wide network; (6) new design which can be used for balloon expandable and/or self-expandable stents; (7) safe seating on the balloon because of round or oval loop material in it's cross section with partly circular or helical configuration; (8) design leads to best collapse resistance and to a tendency towards ring form of the elements in their functional state; (9) new possibility of mixing materials in one stent; and (10) no disintegration (as seen in zig-zag wires).

Further, the stent of the present invention avoids the following listed drawbacks seen with conventional stents: (1) faulty collapse resistance for helical structures or zig-zag patterns made of continuous wire; (2) protruding wires in continuous wire wrappings, especially curves; (3) sharp edges if manufactured of tube sections; (4) stiffness of most stents which are cut of tube sections; (5) stiffness because of too long longitudinal wires in zig-zag wires; (6) tapping of the free stent ends and therefore clutching of the stent and loss of the stent in case of wire and block stents; (7) too thick of a profile which is necessary for collapse resistance; and (8) disintegration.

Equivalent elements can be substituted for the ones set forth above to achieve the same results in the same manner. And, equivalent steps for manufacturing can be employed for the ones set forth above to achieve the same results in the same manner.

What is claimed is:

1. A tubular stent comprising a series of at least three circumferentially arranged circular closed loop elements (1) cut from wire or from flat or tubular material, each of said loop elements having only one major longitudinal axis (2) having a predetermined length and one minor circumferential axis (3) having a predetermined length wherein said loops are aligned with their respective major axis in a parallel manner and their minor axis perpendicular to the longitudinal axis of the stent, each of said closed loop elements being connected to each circumferentially adjacent closed loop element at a discrete point (4) on the loop at the midportion of each major axis between adjacent loops so that each closed loop element has two opposing connecting points, the loop elements arranged circumferentially around a cylindrical member (5) such that the series of closed loop elements form a tubular segment having a proximal and a distal end and a tubular diameter.

2. The stent of claim 1 wherein upon expansion the minor axis (3) of each loop increases in length and the tubular segment assumes an expanded diameter.

3. The stent of claim 1 wherein each of said closed loop elements (1) is symmetrical about the major and minor axis (2 and 3) as in an ellipse.

4. A stent made of a series of closed circular loop elements (1) cut from wire or from tubular or flat material, each of said closed loop elements (1) having a major longitudinal and a minor circumferential axis (2 and 3) each of a predetermined length and wherein said loop elements, (1) are connected to each other at a discrete point (4) on the loops at the midpoint of the major longitudinal axis between adjacent loops to form a chain of closed loop elements and wherein the series of loop elements is arranged helically around a cylindrical member such that the series of loop elements forms a tubular segment with a proximal and distal end and having a tubular diameter.

5. The stent of claim 4, wherein only the first loop and the last loop of the helically arranged chain of loop elements are connected to an adjacent loop element on an adjacent helical turn.

6. The stent of claim 5, wherein at least two loops of adjacent helical turns are connected to the neighboring loop along the longitudinal axis of the stent by a connecting element (6).

7. The stent of claim 6 wherein the connection to the neighboring loop is between the connecting points (4*a,* 4*b*) of the helically arranged loop elements.

8. The stent of claim 4 wherein the stent is self-expandable.

9. The stent of claim 8, wherein the stent is held in its non-expanded state by a mechanism (14) which exerts longitudinal or circumferential traction said helically structured stent assuming its expanded state upon release of such restraining tensile mechanism.

10. The stent of claim 4, wherein upon expansion the length of the minor axis (3) of each closed loop element increases and the tubular segment assumes an expanded diameter.

11. The stent of claim 4 wherein the loop elements are elliptic.

12. The stent of claim 4 wherein the closed loop elements (1) are interconnected at a discrete point (4) at their midportion to form a chain.

13. The stent of claim 4 wherein the closed loop elements (1) in their unexpanded state are interconnected at a discrete point on the loop at a midportion of the major longitudinal axis to form a chain at discrete points (4") outside of the midportion of the major longitudinal axis.

14. The stent of claim 4 wherein the stent is expandable by a balloon.

* * * * *